United States Patent [19]
Wei et al.

[11] Patent Number: 6,077,939
[45] Date of Patent: Jun. 20, 2000

[54] METHODS AND KITS FOR MAKING POLYPEPTIDES HAVING A SINGLE COVALENTLY BOUND N-TERMINAL WATER-SOLUBLE POLYMER

[75] Inventors: Ziping Wei, Belle Mead; Sunitha Menon-Rudolph, Willingboro; Pradip Ghosh-Dastidar, Gladstone, all of N.J.

[73] Assignee: Ortho-McNeil Pharmaceutical, Inc., Raritan, N.J.

[21] Appl. No.: 08/905,310

[22] Filed: Aug. 4, 1997

[51] Int. Cl.[7] .............................. C07K 1/00; A01N 37/18; A61K 38/00
[52] U.S. Cl. .......................... 530/402; 530/300; 530/345; 530/350; 514/2
[58] Field of Search ................................ 514/2; 530/350

[56] References Cited

U.S. PATENT DOCUMENTS 4,835,260  5/1989  Shoemaker .............................. 530/397

FOREIGN PATENT DOCUMENTS

| 427189 A1 | 5/1991 | European Pat. Off. . |
| 668351 | 8/1995 | European Pat. Off. . |
| WO 90/12874 | 11/1990 | WIPO . |
| WO 94/25055 | 11/1991 | WIPO . |
| 9216555 | 10/1992 | WIPO . |
| 9425055 | 11/1994 | WIPO . |
| WO 94/28024 | 12/1994 | WIPO . |

OTHER PUBLICATIONS

Knauf, M.J. et al., J. Biol. Chem 1988, 263, 15,064.
Tsutsumi, Y. et al., J. Controlled Release 1995, 33, 447.
Kita, Y. et al., Drug Des. Delivery 1990, 6, 157.
Abuchowski, A., et al., J. Biol. Chem 1977, 252, 3,582.
Beauchamp, C.O. et al., Anal. Biochem. 1983, 131, 25.
Chen, R. et al.;., Biochim. Biophy. Acta 1981, 660, 293.
Felix A. M. et al., Int. J. Peptide Protein Res. 1995, 46, 253.
Zalipsky, S. et al., Bioconj. Chem. 1995, 6, 705.
Schwarz, A. et al., Methods Enzymol. 1990, 184, 160.
Rose, K. et al., Bioconjugate Chem. 1991, 2, 154.
Gaertner, H.F. et al., J. Biol. Chem. 1994, 269, 7224.
Goodson, R. J. et al., Bio/Technology 1990, 8, 343.
Urrutiogoity, M. et al., Biocatalysis 1989, 2, 145.
Rush, R.S. et al., Anal. Chem. 1995, 67, 1442.
Linsley, K. B. et al., Anal. Biochem. 1994, 219, 207.
Bittorf, T., Jaster, R. and Brock, J. (1993) FEBS Letts. 336: 133–136.
Chern, Y., Chung, T., and Sytkowski, A.J. (1991) Eur. J. Biochem. 202: 225–229.
Funakoshi, A., Muta, H., Baba, T. and Shimizu, S. (1993) Biochem. Biophys. Res. Commun. 195: 717–722.
Grodberg, J., Davis, K. L. and Sytkowski, A.J. (1993) Eur. J. Biochem. 218: 597–601.
Coates, P.M. et al., Nature, 1961, 191, 1065.

*Primary Examiner*—Avis M. Davenport
*Attorney, Agent, or Firm*—Alan J. Morrison

[57] ABSTRACT

This invention provides compositions consisting essentially of a polypeptide and a water-soluble polymer covalently bound thereto at the N-terminal α-carbon atom via a hydrazone or reduced hydrazone bond, or an oxime or reduced oxime bond. This invention also provides methods of making the instant compositions, pharmaceutical compositions comprising same, and kits for use in preparing same.

11 Claims, 10 Drawing Sheets

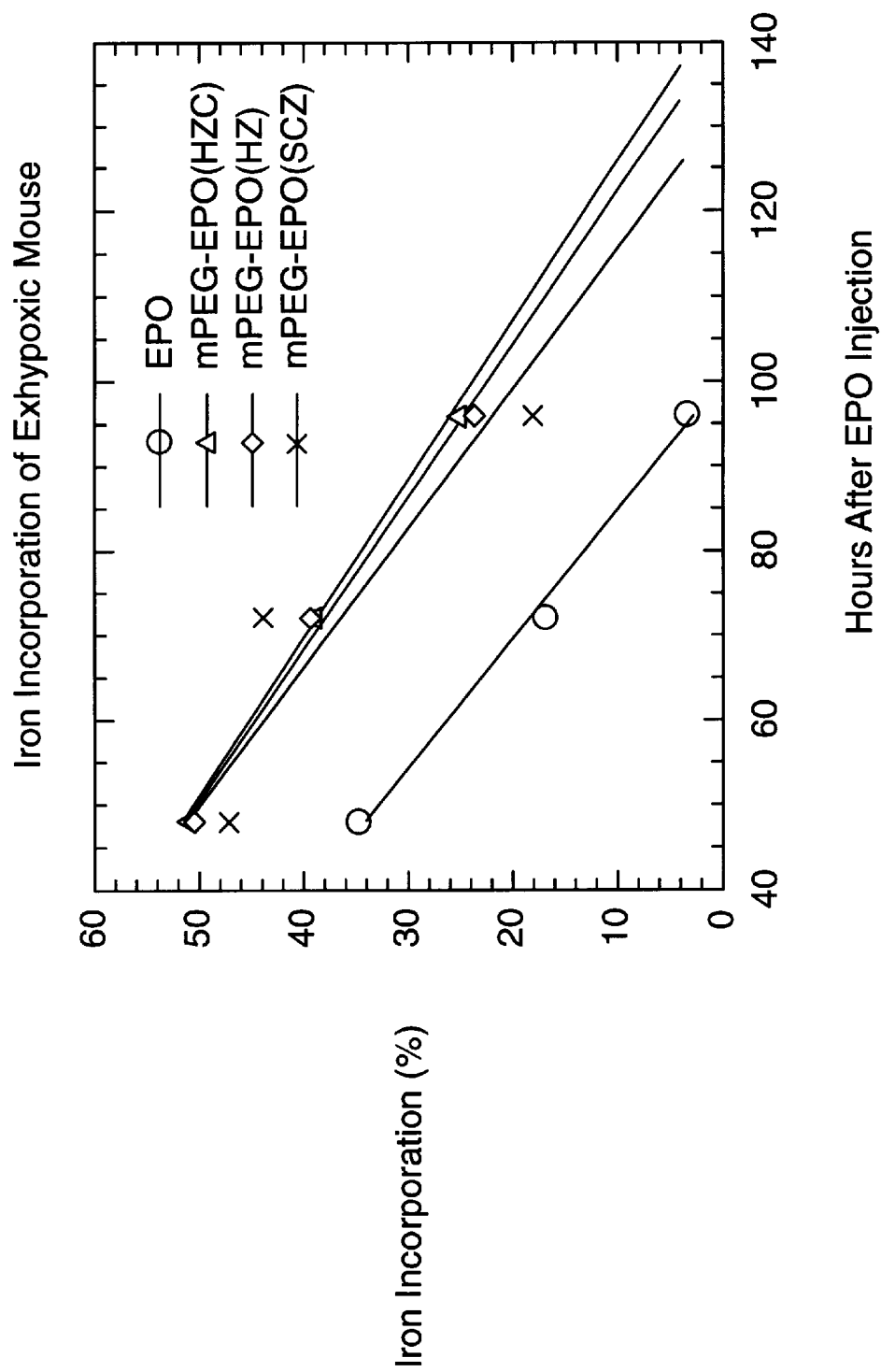

METHODS AND KITS FOR MAKING POLYPEPTIDES HAVING A SINGLE COVALENTLY BOUND N-TERMINAL WATER-SOLUBLE POLYMER

FIELD OF THE INVENTION

The instant invention relates to polypeptides which have bound at their N-termini a single, water soluble polymer. These polypeptides have properties which render them advantageous for use as pharmaceutical and diagnostic agents. The invention also relates to methods of making these polypeptides, and related pharmaceutical compositions and kits.

BACKGROUND OF THE INVENTION

Throughout this application, various publications are cited. The disclosure of these publications is hereby incorporated by reference into this application to describe more fully the state of the art to which this invention pertains.

In recent years, non-antigenic water-soluble polymers, such as polyethylene glycol ("PEG"), have been used for the covalent modification of polypeptides of therapeutic and diagnostic importance. For example, covalent attachment of PEG to therapeutic polypeptides such as interleukins (Knauf, M. J. et al., *J. Biol. Chem.* 1988, 263, 15,064; Tsutsumi, Y. et al., *J. Controlled Release* 1995, 33, 447), interferons (Kita, Y. et al., *Drug Des. Delivery* 1990, 6, 157), catalase (Abuchowski, A. et al., *J. Biol. Chem.* 1977, 252, 3, 582), superoxide dismutase (Beauchamp, C. O. et al., *Anal. Biochem.* 1983, 131, 25), and adenosine deaminase (Chen, R. et al., *Biochim. Biophy. Acta* 1981, 660, 293), has been reported to extend their half life in vivo, and/or reduce their immunogenicity and antigenicity.

However, such methods have serious drawbacks. Specifically, in most instances, PEG molecules are attached through amino groups on polypeptides using methoxylated PEG ("mPEG") having different reactive moieties. Such polymers include mPEG-succinimidyl succinate, mPEG-succinimidyl carbonate, mPEG-imidate, and mPEG-cyanuric chloride. The attachment using these polymers was usually non-specific, i.e., occurring at various amino groups on the polypeptides in a random fashion, and not exclusively at a particular amino group. Such non-specific attachment may modify amino acid residues at active sites in such a manner as to eliminate the biological activity of the polypeptides. Also, the resultant conjugates may contain a heterogeneous mixture of modified polypeptide, which is undesirable for pharmaceutical use.

To overcome these problems, it was desirable to site-specifically attach a polymer to a polypeptide. For the polypeptide, doing so would preserve biological activity, prolong blood circulating time, reduce immunogenicity, increase aqueous solubility, and enhance resistance to protease digestion. Site-specific pegylation at the N-terminus, side chain and C-terminus of a potent analog of growth hormone-releasing factor has been performed through solid-phase synthesis(Felix, A. M. et al., *Int. J. Peptide Protein Res.* 1995, 46, 253). Since the specific pegylation was accomplished during assembly of the peptide on a resin, the method can not be applied to an existing peptide.

An additional method used involved attaching a peptide to extremities of liposomal surface-grafted PEG chains in a site-specific manner through a reactive aldehyde group at the N-terminus generated by sodium periodate oxidation of N-terminal threonine (Zalipsky, S. et al., *Bioconj. Chem.* 1995, 6, 705). However, this method is limited to polypeptides with N-terminal serine or threonine residues.

Enzyme-assisted methods for introducing activated groups specifically at the C-terminus of a polypeptide have also been described (Schwarz, A. et al., *Methods Enzymol.* 1990, 184, 160; Rose, K. et al., *Bioconjugate Chem.* 1991, 2, 154; Gaertner, H. F. et al., *J. Biol. Chem.* 1994, 269, 7224). Typically, these active groups can be hydrazide, aldehyde, and aromatic-amino groups for subsequent attachment of functional probes to polypeptides. However, since the methods are based on the specificity of proteases, they require extreme caution, and the scope of their application is limited.

Site-specific mutagenesis is a further approach which has been used to prepare polypeptides for site-specific polymer attachment. WO 90/12874 describes the site-directed pegylation of proteins modified by the insertion of cysteine residues or the substitution of other residues for cysteine residues. This publication also describes the preparation of mPEG-erythropoietin ("mPEG-EPO") by reacting a cysteine-specific mPEG derivative with a recombinantly introduced cysteine residue on EPO. Similarly, interleukin-2 was pegylated at its glycosylation site after site-directed mutagenesis (Goodson, R. J. et al., *Bio/Technology* 1990, 8, 343).

Glycoproteins provide carbohydrates as additional target sites for modification. The enzyme peroxidase has been modified with PEG-diamine through its carbohydrate moiety (Urrutiogoity, M. et al., *Biocatalysis* 1989, 2, 145). WO 94/28024 describes the methods for preparing mPEG-EPO through periodate-oxidized carbohydrate. The chemistry involved was hydrazone formation by reacting mPEG-hydrazide with aldehyde groups of the carbohydrate moiety on EPO. This type of modification generates reactive aldehyde groups through an oxidation step, which potentially can oxidize various types of sugar residues in the carbohydrate moiety and some amino acid residues in the polypeptide, such as methionine. Another disadvantage of this method stems from the heterogeneity of the carbohydrate moieties of EPO. EPO expressed from Chinese hamster ovary cells has four carbohydrate chains, which include three N-linked chains at asparagines 24, 38, and 83 and one O-linked chain at serine 126. A total of 52 different N-linked, and at least 6 O-linked, oligosaccharide structures have been identified (Rush, R. S. et al., *Anal. Chem.* 1995, 67, 1442; Linsley, K. B. et al., *Anal. Biochem.* 1994, 219, 207). Accordingly, it is difficult to control the number of, or attachment sites of, polymer molecules when modifying EPO or other protein via its carbohydrate chains.

In short, the methods in the art for attaching a water-soluble polymer to a polypeptide suffer from serious drawbacks. These drawbacks include the following: (a) a lack of precision, both stoichiometrically and with respect to the situs of attachment; (b) the need to perform difficult and labor-intensive techniques such as site-specific mutagenesis; (c) the need to use solid-phase peptide synthesis concurrently with polymer attachment, instead of attaching a polymer to a pre-existing polypeptide; and (d) the rigid requirement that the identity of the N-terminal amino acid residue be threonine or serine.

For some time, there has existed a need for a general method of site-specifically attaching a water-soluble polymer to the N-terminal amino acid residue of a polypeptide, which method does not suffer from the above-identified drawbacks. However, no such method exists.

SUMMARY OF THE INVENTION

This invention provides two compositions of matter. The first composition of matter consists essentially of a polypeptide and a water-soluble polymer covalently bound thereto at the N-terminal α-carbon atom of the polypeptide via a hydrazone bond or reduced hydrazone bond, with the proviso that (a) the polymer has a molecular weight of from about 200 to about 200,000 daltons, (b) the natural function of the polypeptide is not eliminated upon removal of its N-terminal α-amino group, and (c) the polypeptide's N-terminal amino acid residue is not serine or threonine.

The second composition of matter consists essentially of a polypeptide and a water-soluble polymer covalently bound thereto at the N-terminal α-carbon atom of the polypeptide via an oxime bond or reduced oxime bond, with the proviso that (a) the polymer has a molecular weight of from about 200 to about 200,000 daltons, and (b) the natural function of the polypeptide is not eliminated upon removal of its N-terminal α-amino group.

This invention also provides four methods of covalently binding a water-soluble polymer to the N-terminal α-carbon atom of a polypeptide. The first method, which binds the polymer to the carbon atom via a hydrazone bond, comprises the steps of
(a) contacting the polypeptide with (i) glyoxylate ion or derivative thereof at a concentration of from about 0.1 M to about 2.0 M, (ii) a transition metal ion at a concentration of from about 10 µM to about 1 M, and (iii) a Lewis base at a concentration of from about 10 mM to about 10 M, at a pH of from about 3.0 to about 8.0 and a temperature of from about 0° C. to about 100° C., so as to form a transaminated polypeptide having an N-terminal α-carbonyl group; and
(b) contacting the transaminated polypeptide, at a pH of from about 1.0 to about 7.5, with a water-soluble polymer having a moiety covalently bound thereto which reacts with the transaminated polypeptide's N-terminal α-carbonyl group to form a hydrazone bond, thereby covalently binding the polymer to the N-terminal α-carbon atom of the polypeptide via a hydrazone bond, with the proviso that the polymer has a molecular weight of from about 200 to about 200,000 daltons, and the natural function of the polypeptide is not eliminated upon removal of its N-terminal α-amino group.

The second method, which binds the polymer to the carbon atom via an oxime bond, comprises the steps of
(a) contacting the polypeptide with (i) glyoxylate ion or derivative thereof at a concentration of from about 0.1 M to about 2.0 M, (ii) a transition metal ion at a concentration of from about 10 µM to about 1 M, and (iii) a Lewis base at a concentration of from about 10 mM to about 10 M, at a pH of from about 3.0 to about 8.0 and a temperature of from about 0° C. to about 100° C., so as to form a transaminated polypeptide having an N-terminal α-carbonyl group; and
(b) contacting the transaminated polypeptide, at a pH of from about 1.0 to about 7.5, with a water-soluble polymer having a moiety covalently bound thereto which reacts with the transaminated polypeptide's N-terminal α-carbonyl group to form an oxime bond, thereby covalently binding the polymer to the N-terminal α-carbon atom of the polypeptide via an oxime bond, with the proviso that the polymer has a molecular weight of from about 200 to about 200,000 daltons, and the natural function of the polypeptide is not eliminated upon removal of its N-terminal α-amino group.

The third method comprises the steps of the first method, as well as a further step of reducing the hydrazone bond formed in step (b). The fourth method comprises the steps of the second method, as well as a further step of reducing the oxime bond formed in step (b).

This invention also provides a pharmaceutical composition which comprises an effective amount of the instant first or second composition, and a pharmaceutically acceptable carrier.

Finally, this invention provides kits for use in preparing the instant compositions. The first kit, for preparing the first instant composition, comprises the following:
(a) a glyoxylate ion or derivative thereof;
(b) a transition metal ion;
(c) a Lewis base; and
(d) a water-soluble polymer having a molecular weight of from about 200 to about 200,000 daltons, and having a moiety covalently bound thereto which reacts with a transaminated polypeptide's N-terminal α-carbonyl group to form a hydrazone bond, thereby covalently binding the polymer to the N-terminal α-carbon atom of the polypeptide.

The second kit, for use in preparing the second instant Composition, comprises the following:
(a) a glyoxylate ion or derivative thereof;
(b) a transition metal ion;
(c) a Lewis base; and
(d) a water-soluble polymer having a molecular weight of from about 200 to about 200,000 daltons, and having a moiety covalently bound thereto which reacts with a transaminated polypeptide's N-terminal α-carbonyl group to form an oxime bond, thereby covalently binding the polymer to the N-terminal α-carbon atom of the polypeptide.

BRIEF DESCRIPTION OF THE FIGURES

FIG. 7 shows a graph of the results of an exhypoxic mouse bioassay for mPEG-EPO with hydrazone bonds formed using hydrazine carboxylate (HZC), hydrazide (HZ) and semicarbazide (SCZ) moieties.

DETAILED DESCRIPTION OF THE INVENTION

Figure 1:
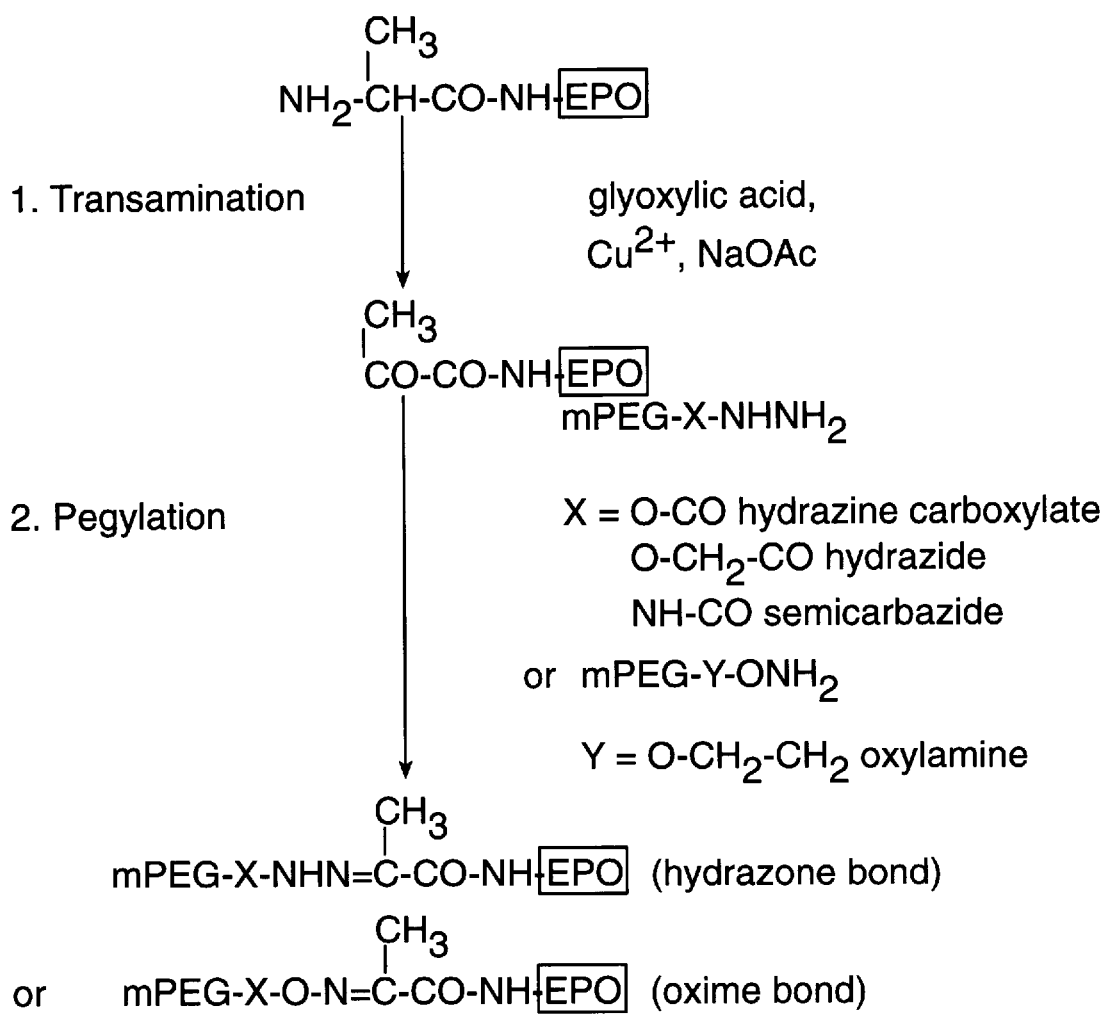
FIG. 1 shows a scheme for preparing N-terminal modified EPO. This is a two-step reaction: transamination and pegylation. Four mPEG5000 (i.e., mPEG having a m.w. of 5000 daltons) derivatives with hydrazine carboxylate (HZC), hydrazide (HZ), semicarbazide (SCZ) and oxylamine functional groups were used.

This invention provides two compositions of matter. The first composition of matter consists essentially of a polypeptide and a water-soluble polymer covalently bound thereto at the N-terminal α-carbon atom of the polypeptide via a hydrazone bond or reduced hydrazone bond, with the proviso that (a) the polymer has a molecular weight of from about 200 to about 200,000 daltons, (b) the natural function of the polypeptide is not eliminated upon removal of its N-terminal α-amino group, and (c) the polypeptide's N-terminal amino acid residue is not serine or threonine.

The second composition of matter consists essentially of a polypeptide and a water-soluble polymer covalently bound thereto at the N-terminal α-carbon atom of the polypeptide via an oxime bond or reduced oxime bond, with the proviso that (a) the polymer has a molecular weight of from about 200 to about 200,00 daltons, and (b) the natural function of the polypeptide is not eliminated upon removal of its N-terminal α-amino group.

As used herein, "polypeptide" includes both peptides and proteins. "Peptide" means a polypeptide of fewer than 10 amino acid residues in length, and "protein" means a polypeptide of 10 or more amino acid residues in length. In this invention, the polypeptides may be naturally occurring or recombinant (i.e. produced via recombinant DNA technology), and may contain mutations (e.g. point, insertion and deletion mutations) as well as other covalent modifications (e.g. glycosylation and labeling [via biotin, streptavidin, fluoracine, and radioisotopes such as $I^{131}$) Moreover, each instant composition may contain more than a single polypeptide, i.e., each may be a monomer (one polypeptide bound to a polymer) or a multimer (two or more polypeptides bound to a polymer or to each other).

Polypeptides include, by way of example, monoclonal and polyclonal antibodies, cytokines such as M-CSF and GM-CSF, lymphokines, IL-2, IL-3, growth factors such as PDGF and EGF, peptide hormones such as hGH, EPO and derivatives thereof, blood clotting factors such as Factor VIII, immunogens, enzymes, enzyme inhibitors, and other ligands. In the preferred embodiment of the instant compositions, the poplypeptide is EPO or derivative thereof. The EPO may be naturally occurring or recombinant. Derivatives of EPO include, but are not limited to, the polypeptides GGLYLCRFGPVTWDCGYKGG, GGTYSCHFGPLTWVCK-
PQGG, GGDYHCRMGPLTWVCKPLGG, VGNYMCHFGPIT-
WVCRPGGG, GGVYACRMGPITWVCSPLGG, VGNYMAH-
MGPITWVCRPGG, GGTYSCHFGPLTWVCKPQ,
GGLYACHMGPMTWVCQPLRG, TIAQYICYMGPETWE-
CRPSPKA, YSCHFGPLTWVCK, and YCHFGPLTWVC, as well as the mutants listed in Table 1 below.

TABLE 1

| Mutation | Activity relative to wt‡ | Reference |
|---|---|---|
| L5S | +/− | 9 |
| L5S/W51S/M54S/V82S/W88S/L112A/A124S/A125S | +/− | 9 |
| S9A | ++++ | 3 |

TABLE 1-continued

| Mutation | Activity relative to wt‡ | Reference |
|---|---|---|
| R10A | ++++ | 3 |
| E13A | ++++ | 3 |
| R14L | ++++ | 3 |
| R14A | ++ | 3 |
| L17A | ++++ | 3 |
| E18A | ++++ | 3 |
| K20A | ++++ | 3 |
| E21A | ++++ | 3 |
| N24Q | ++ | 1 |
| N24Q/N83Q | + | 1 |
| N24Q/N38Q/N83Q | +++ | 1 |
| C29Y/C33Y | ++++ | 3 |
| A30S/L35S | +++ | 9 |
| A30S/A124S/A125S | ++ | 9 |
| C33P/R139C | ++++ | 7 |
| L35S/A124S/A125S | ++ | 9 |
| N38Q | ++ | 1 |
| N38Q/N83Q | ++++ | 1 |
| V41S | +/− | 9 |
| K45A | ++++ | 3 |
| F48S | ++++ | 3 |
| Y49S | ++++ | 3 |
| A50S | ++++ | 3 |
| W51S | ++++ | 3 |
| W51S/V144S | + | 9 |
| W51S/V82S/W88S | ++ | 9 |
| W51S/V82S/W88S/V144N | ++ | 9 |
| W51S/V82S/W88S/L112A/I119A A124S/A125S | +++ | 9 |
| W51S/M54S/V82S/W88S/A124S A125S | ++ | 9 |
| W51S/M54S/V82S/W88S/L112A A124S/A125S | + | 9 |
| W51S/M54S/V82S/W88S/L112A A124S/A125S/L130A | +++ | 9 |
| W51S/M54S/V82S/W88S/I119A A124S/A125S | + | 9 |
| W51S/M54S/V82S/W88S/L112A I119A/A124S/A125S | +++ | 9 |
| W51S/M54S/V82S/W88S/A124S A125S/L130A | +++ | 9 |
| W51S/V82S/W88S/A125S/A125S L130A | +++ | 9 |
| K52S | ++++ | 3 |
| M54L | ++++ | 10 |
| M54S/V56S | ++++ | 9 |
| W57S/V82S/W88S/L112A/I119A A124S/A125S | +++ | 9 |
| E62A | ++++ | 3 |
| W64A | ++++ | 3 |
| Q65A | ++++ | 3 |
| G66A | ++++ | 3 |
| L69A | ++++ | 3 |
| L69N | ++++ | 4 |
| S71A | +++ | 3 |
| A73G | ++++ | 3 |
| R76A | ++++ | 3 |
| V82S | +/− | 9 |
| V82S/W88S/V144N | ++ | 9 |
| V82S/W88S/A124S/A125S | ++++ | 9 |
| N83Q | ++ | 9 |
| Q92A | ++++ | 3 |
| L93A | ++++ | 3 |
| K97A | ++++ | 3 |
| S100A | ++++ | 3 |
| G101A | ++++ | 3 |
| L102A | ++++ | 8 |
| R103A | ++ | 2 |
| S104A | ++ | 3 |
| S104N | +/− | 6 |
| L105A | ++ | 8 |
| L105F | +/− | 6 |
| T106A | ++++ | 3 |
| T107A | +++ | 8 |
| L108A | ++ | 3 |
| L109A | +++ | 8 |
| L112A | +/− | 9 |

TABLE 1-continued

| Mutation | Activity relative to wt‡ | Reference |
|---|---|---|
| L112A/I119S/L130A/I133A | ++++ | 9 |
| P122Q | +/− | 6 |
| A124P/A125T | ++++ | 4 |
| A125T | ++++ | 4 |
| A125N/A127S | ++++ | 4 |
| L130A | +/− | 9 |
| D136A | ++++ | 3 |
| R139A | ++++ | 3 |
| K140A | ++++ | 3 |
| R143A | ++++ | 3 |
| S146A | ++++ | 3 |
| N147A | ++++ | 3 |
| R150A | +++ | 3 |
| K152A | ++ | 3 |
| L153A | +++ | 3 |
| K154A | ++++ | 3 |
| L155A | ++++ | 3 |
| Y156A | ++ | 3 |
| T157A | ++++ | 3 |
| G158A | ++++ | 3 |
| E159A | ++++ | 3 |
| R162K/T163D/G164E/D165L | ++ | 3 |
| R162H/T163H/G164H/D165H/R166H/(167)H | ++++ | 3 |
| Æ2–5 | ++ | 3 |
| Æ13–17 | ++++ | 2 |
| Æ32–36 | ++ | 3 |
| Æ43–47 | ++ | 3 |
| Æ53–57 | ++ | 3 |
| Æ78–82 | + | 3 |
| Æ111–119 | +++ | 3 |
| Æ115–121 | +++ | 2 |
| Æ120–122 | ++++ | 5 |
| Æ123–125 | ++++ | 5 |
| Æ126–129 | +++ | 5 |
| Æ163–166 | ++++ | 3 |
| K116 (insertion of LISEEDL) | ++++ | 3 |

‡Relative to wildtype is defined as follows:
++++ = wildtype or better activity
+++ = c.a. 75% of wildtype activity
++ = c.a. 50% of wildtype activity
+ = c.a. 25% of wildtype activity
+/− = mutant EPO reported to be active, however, data not complete for assessment of activity relative to wildtype.
Cited References
(1) Akai, K., Yamaguchi, K. and Ueda, M., Modified forms of human erythropoietin and DNA sequences encoding genes which can express them, EP 0427 189 Al.
(2) Bittorf, T., Jaster, R. and Brock, J. (1993) FEBS Letts. 336: 133–136.
(3) Results of Bunn, H. F., et al.
(4) Byrne, T. E. and Elliot, S. G., Erythropoietin isoforms, EP 0 668 351 Al.
(5) Chern, Y., Chung, T., and Sytkowski, A. J. (1991) Eur. J. Biochem. 202: 225–229.
(6) Funakoshi, A., Muta, H., Baba, T. and Shimizu, S. (1993) Biochem. Biophys. Res. Commun. 195: 717–722.
(7) Okasinski, G., Devries, P. J., Mellovitz, B. S., Meuth, J. L. and Schaefer, V. G., Erythropoietin analog compositions and methods, WO 94/25055.
(8) Grodberg, J., Davis, K. L.; and Sytkowski, A. J. (1993) Eur. J. Biochem. 218: 597–601.
(9) Results of Pulito, V. et al.
(10) Shoemaker, C. B., Erythropoietin composition, U.S. Pat. No. 4,835, 260.

As used herein, the "natural function" of a polypeptide means its function prior to covalent modification of its N-terminal α-amino group. Natural functions include, for example, enzymatic activity, receptor binding (e.g. antibodies), ligand binding, and immunogenicity.

The instant methods described more fully below cause the loss of the N-terminal α-amino group of the polypeptide being covalently modified. Accordingly, the polypeptide must have a primary structure such that its natural function is preserved after covalent modification, and cannot be eliminated. The natural function of the polypeptide is "eliminated" by the removal of its N-terminal α-amino group if such removal reduces, by more than 99%, the capacity of the polypeptide to perform its natural function. In one embodiment, the removal does not reduce the capacity of the polypeptide to perform its natural function by more than 90%. In the preferred embodiment, the removal does not reduce the capacity of the polypeptide to perform its natural function by more than 50%.

As used herein, a "hydrazone bond" is a bond comprising the covalent structure NH—N=C, an "oxime bond" is a bond comprising the covalent structure O—N=C, a "reduced hydrazone bond" is a bond comprising the covalent structure NH—NH—C, and a "reduced oxime bond" is a bond comprising the covalent structure O—NH—C. Compounds containing reduced hydrazone and oxime bonds are provided herein, since these bonds possess greater chemical stability.

As discussed above, methods are known in the art for binding water-soluble polymers to the N-terminal α-carbon atom of a polypeptide via a hydrazone bond so long as the N-terminal amino acid residue is serine or threonine. These known methods will not work on polypeptides having any other N-terminal residue. Although these known methods differ fundamentally from the instant methods, they do result in N-terminal serine and threonine polypeptides having a polymer bound at the N-terminal α-carbon atom via a hydrazone bond. For this reason, the instant first composition does not encompass a polypeptide bound to a polymer via a hydrazone bond, where the polypeptide's N-terminal amino acid residue is serine or threonine.

The water-soluble polymers used in the instant invention include, but are not limited to, (a) dextran and dextran derivatives, including dextran sulfate, cross linked dextrin, and carboxymethyl dextrin; (b) cellulose and cellulose derivatives, including methylcellulose and carboxymethyl cellulose; (c) starch and dextrines, and derivatives thereof; (d) polyalkylene glycol and derivatives thereof, including PEG, mPEG, PEG homopolymers, polypropylene glycol homopolymers, copolymers of ethylene glycol with propylene glycol, wherein said homopolymers and copolymers are unsubstituted or substituted at one end with an alkyl group; (e) heparin and fragments of heparin; (f) polyvinyl alcohol and polyvinyl ethyl ethers; (g) polyvinylpyrrolidone; (h) a,b-poly[(2-hydroxyethyl)-DL-aspartamide; and (i) polyoxyethylated polyols. These polymers can be linear, branched, or star-shaped with a wide range of molecular weight. In the preferred embodiment, the polymer is mPEG.

When the instant compositions are to be used as pharmaceuticals, the polymer is non-toxic. Furthermore, when a polymer is said to have a given molecular weight, that molecular weight may only be approximate, reflecting the average molecular weight of a population of polymer molecules differing with respect to one another in regard to the number of subunits present in each molecule.

In one embodiment, the PEG or derivative thereof has a molecular weight of from about 700 to about 20,000 daltons. In the preferred embodiment, the PEG or derivative thereof has a molecular weight of about 5,000 daltons. Also, in the preferred embodiment of the instant compositions, the polypeptide is EPO, and the polymer is mPEG having a molecular weight of about 5,000 daltons.

This invention also provides four methods of covalently binding a water-soluble polymer to the N-terminal a-carbon atom of a polypeptide. The first method, which binds the polymer to the carbon atom via a hydrazone bond, comprises the steps of (a) contacting the polypeptide with (i) glyoxylate ion or derivative thereof at a concentration of from about 0.1 M to about 2.0 M, (ii) a transition metal ion at a concentration of from about 10 μM to about 1 M, and (iii) a Lewis base at a concentration of from about 10 mM to about 10 M, at a pH of from about 3.0 to about 8.0 and a temperature of from about 0° C. to about 100° C., so as to form a transaminated polypeptide having an N-terminal α-carbonyl group; and (b) contacting the transaminated polypeptide, at a pH of from about 1.0 to about 7.5, with a water-soluble polymer having a moiety covalently bound thereto which reacts with the transaminated polypeptide's N-terminal α-carbonyl group to form a hydrazone bond, thereby covalently binding the polymer to the N-terminal α-carbon atom of the polypeptide via a hydrazone bond, with the proviso that the polymer has a molecular weight of from about 200 to about 200,000 daltons, and the natural function of the polypeptide is not eliminated upon removal of its N-terminal α-amino group.

The second method, which binds the polymer to the carbon atom via an oxime bond, comprises the steps of (a) contacting the polypeptide with (i) glyoxylate ion or derivative thereof at a concentration of from about 0.1 M to about 2.0 M, (ii) a transition metal ion at a concentration of from about 10 μM to about 1 M, and (iii) a Lewis base at a concentration of from about 10 mM to about 10 M, at a pH of from about 3.0 to about 8.0 and a temperature of from about 0° C. to about 100° C., so as to form a transaminated polypeptide having an N-terminal α-carbonyl group; and (b) contacting the transaminated polypeptide, at a pH of from about 1.0 to about 7.5, with a water-soluble polymer having a moiety covalently bound thereto which reacts with the transaminated polypeptide's N-terminal α-carbonyl group to form an oxime bond, thereby covalently binding the polymer to the N-terminal α-carbon atom of the polypeptide via an oxime bond, with the proviso that the polymer has a molecular weight of from about 200 to about 200,000 daltons, and the natural function of the polypeptide is not eliminated upon removal of its N-terminal α-amino group.

The third method comprises the steps of the first method, as well as a further step of reducing the hydrazone bond formed in step (b). The fourth additional method comprises the steps of the second method, as well as a further step of reducing the oxime bond formed in step (b). The reducing step can be performed by using, for example, sodium borohydride (NaBH$_4$) and sodium cyanoborohydride (NaBH$_3$CN), according to known methods. Glyoxylate ion derivatives include, but are not limited to, glyoxylamide and phenylglyoxyl ions. Transition metal ions include, but are not limited to, cupric, nickel, cobaltous, or zinc ions. Lewis bases include, but are not limited to, acetate and pyridine.

Moieties which react with the transaminated polypeptide's N-terminal α-carbonyl group to form a hydrazone bond include, but are not limited to, hydrazine carboxylate, hydrazine, semicarbazide, hydrazide, thiosemicarbazide, carbonic acid dihydrazide, carbazide, thiocarbazide, and arylhydrazide. Water-soluble polymers with these moieties covalently bound thereto are commercially available. In addition, moieties which react with the transaminated polypeptide's N-terminal α-carbonyl group to form an oxime bond include, but are not limited to, oxylamine. Water-soluble polymers with oxylamine (as well as other oxime-forming moieties) covalently bound thereto are commercially available.

In the preferred embodiment of the instant methods, the pH for step (a) is from about 5.0 to about 7.0, the pH for step (b) is from about 3.0 to about 5.0, and the protein is EPO or derivative thereof.

In one embodiment of the instant methods, the polymer is PEG or derivative thereof. In a further embodiment, the PEG or derivative thereof has a molecular weight of from about 700 to about 20,000 daltons. In the preferred embodiment, the PEG or derivative thereof has a molecular weight of about 5,000 daltons.

In one embodiment of the first method, the moiety bound to the polymer which is reacted with the transaminated polypeptide is hydrazine carboxylate. In the preferred embodiment, the polypeptide is EPO, the polymer is mPEG having a molecular weight of about 5,000 daltons, and the moiety covalently bound to the polymer is hydrazine carboxylate.

In one embodiment of the second method, the moiety bound to the polymer which is reacted with the transaminated polypeptide is oxylamine.

In each of the instant methods, the preferred contacting time for step (a) is from 20 minutes to 2 hours, and for step (b), the preferred contacting time and temperature are from 10 to 50 hours and from 4° C. to room temperature, respectively.

With certain polypeptides, the N-terminus of a polypeptide is "buried", i.e. not exposed to solvents or reagents therein, when the polypeptide is in its native conformation. Reagents such as tetramethylurea or urea may be used to unfold such a polypeptide in order to permit its N-terminal residue to undergo the required reactions of the instant methods.

This invention also provides a pharmaceutical composition which comprises an effective amount of the instant first or second composition, and a pharmaceutically acceptable carrier. By way of example, the instant pharmaceutical composition may comprise an amount of the instant mPEG-EPO effective to treat a subject suffering from anemia.

Pharmaceutically acceptable carriers are well known to those skilled in the art and include, but are not limited to, 0.01–0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

Finally, this invention provides kits for use in preparing the instant compositions. The first kit, for preparing the first instant composition, comprises the following:

(a) a glyoxylate ion or derivative thereof;

(b) a transition metal ion;

(c) a Lewis base; and (d) a water-soluble polymer having a molecular weight of from about 200 to about 200,000 daltons, and having a moiety covalently bound thereto which reacts with a transaminated polypeptide's N-terminal α-carbonyl group to form a hydrazone bond, thereby covalently binding the polymer to the N-terminal α-carbon atom of the polypeptide.

The second kit, for use in preparing the second instant composition, comprises the following:
(a) a glyoxylate ion or derivative thereof;
(b) a transition metal ion;
(c) a Lewis base; and
(d) a water-soluble polymer having a molecular weight of from about 200 to about 200,000 daltons, and having a moiety covalently bound thereto which reacts with a transaminated polypeptide's N-terminal α-carbonyl group to form an oxime bond, thereby covalently binding the polymer to the N-terminal α-carbon atom of the polypeptide.

The reagents in these kits may be packaged in a predetermined quantity, and may be contained in separate compartments. Alternatively, certain reagents may be contained in the same compartment as the constraints of the instant methods permit. Finally, the kits may further comprise reducing reagents for generating reduced hydrazone and oxime bonds according to the instant methods, as well as suitable buffers and reaction vessels.

This invention will be better understood by reference to the Experimental Examples which follow, but those skilled in the art will readily appreciate that the specific experiments detailed are only illustrative of the invention as described more fully in the claims which follow thereafter.

EXPERIMENTAL EXAMPLES

1. Preparation of Transaminated EPO 5 mg of EPO in 20 mM sodium citrate (pH 6.9) and 100 mM NaCl was exchanged to 100 mM sodium acetate (pH 7.0) buffer using Centricon-10 (Amicon, Beverly, Mass.). The final concentrations were adjusted to 1 mg/ml EPO, 2 M sodium acetate, 0.4 M acetic acid, 0.1 M glyoxylic acid, and 10 mM cupric sulfate (pH 5.5) (FIG. 1). The reaction was allowed for 2 hours at room temperature, and was stopped by adding 100 ml of 0.5 M EDTA. Transaminated EPO was purified via a Sephadex G-25 column (Pharmacia, Piscataway, N.J.) using a 100 mM sodium acetate (pH 4.5) buffer.

The extent of transamination was estimated by 2,4-dinitrophenylhydrazine as described in the literature (Fields, R. et al., *Biochem. J.*, 1971, 121, 587). Extinction at 370 nm was measured after the first few minutes and after one hour. The difference in absorbance is proportional to the amount of carbonyl groups present on the EPO molecule. The transaminated EPO was also subjected to amino acid analysis on an ABI 420H system (Applied Biosystems, Foster City, Calif.) using pre-column PITC chemistry. The results indicate that lysine residues, i.e. non-N-terminal residues, were not transaminated.

2. Preparation of mPEG-EPO with mPEG-Hydrazine Carboxylate

Transaminated EPO (1 mg) in 100 mM sodium acetate (pH 4.5) was adjusted to 0.5 M sodium chloride to a final volume of 1 ml, to which 10 mg of mPEG5000 hydrazine carboxylate (Shearwater Polymers, Hunstville, Ala.) was added. The reaction mixture was stirred for 40 hours at room temperature, and purified via a Sephacryl S-200 column (Pharmacia, Piscataway, N.J.) using a 20 mM sodium citrate (7.0) buffer containing 100 mM NaCl. Additionally, 0.1% SDS may be added to the reaction mixture to increase the conjugation yield.

Figure 2:
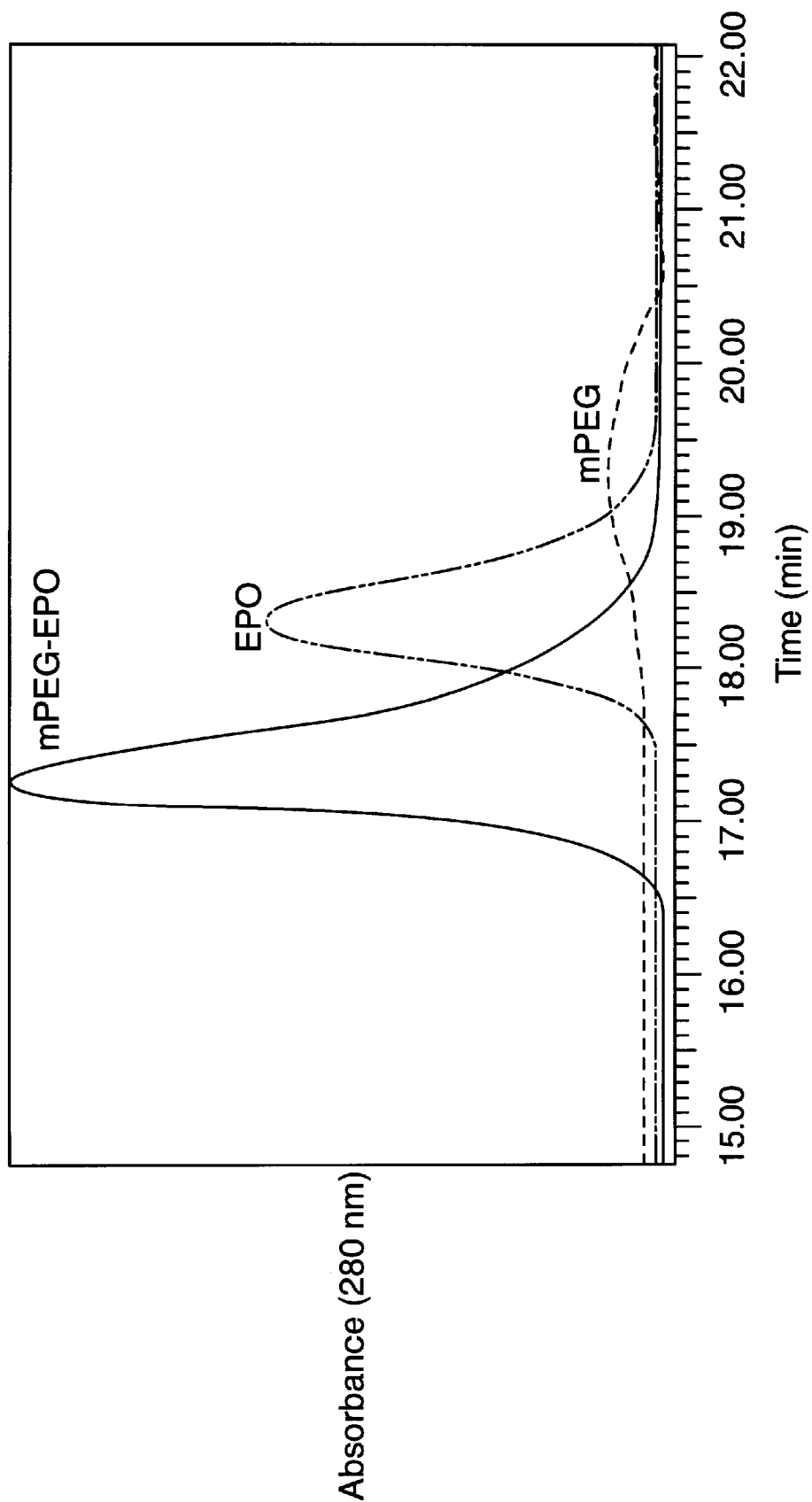
FIG. 2 shows the gel filtration chromatogram of mPEG-EPO with a hydrazone bond formed using a hydrazine carboxylate (HZC) moiety, native EPO, and mPEG5000 hydrazine carboxylate on a TSK G3000SW$_{XL}$ column (7.5× 30 mm). The mobile phase is 20 mM sodium citrate (pH 7.0) containing 100 mM NaCl.

In gel permeation chromatography, the mPEG-EPO conjugate showed a substantially increased molecular weight compared to those of EPO and mPEG5000 hydrazine carboxylate (FIG. 2).

Figure 3A:
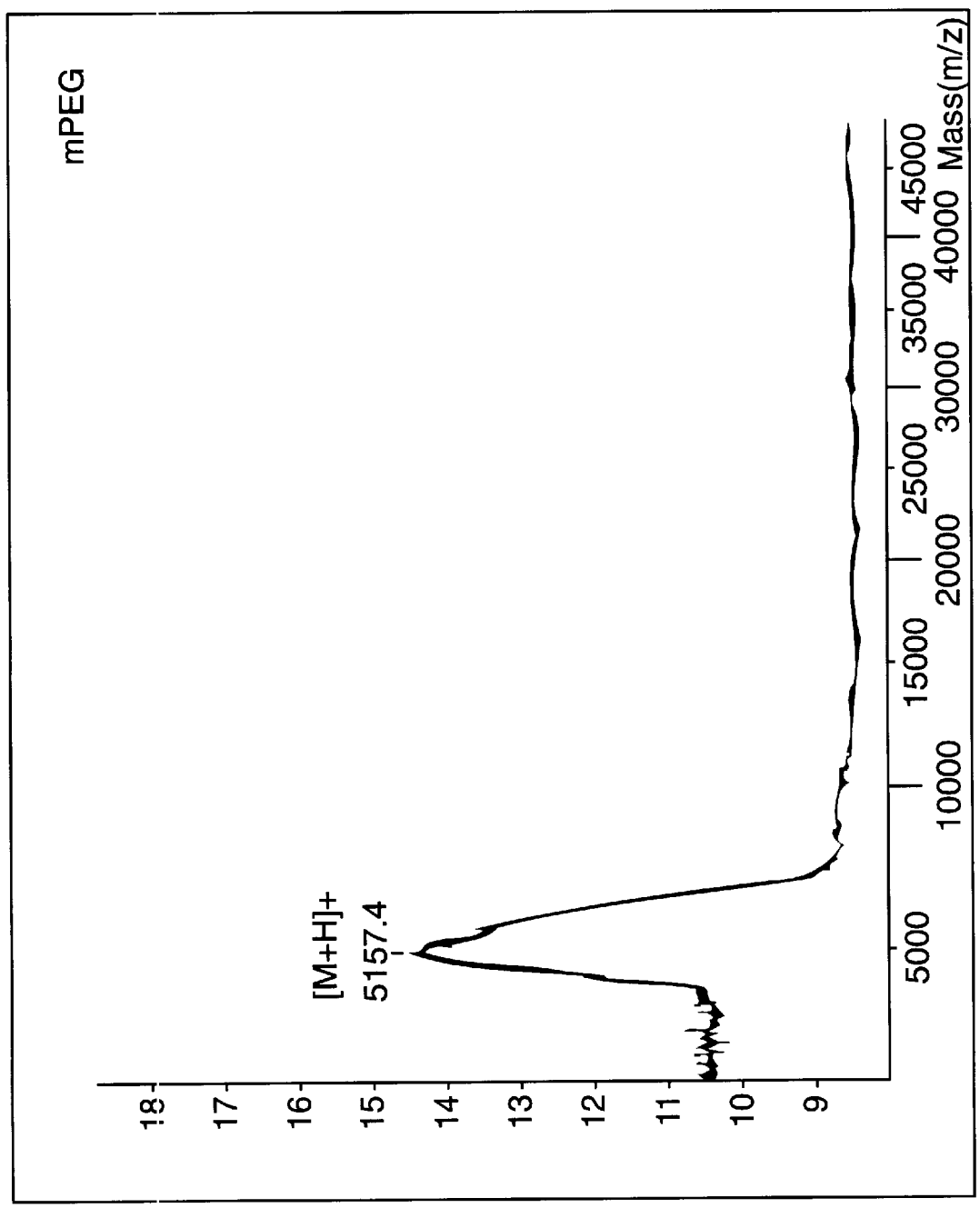
FIG. 3 shows a matrix-assisted laser desorption time-of-flight mass spectra of mPEG5000 hydrazine carboxylate, native EPO, and mPEG-EPO with a hydrazone bond formed using a hydrazine carboxylate (HZC) moiety.
Figure 3B:
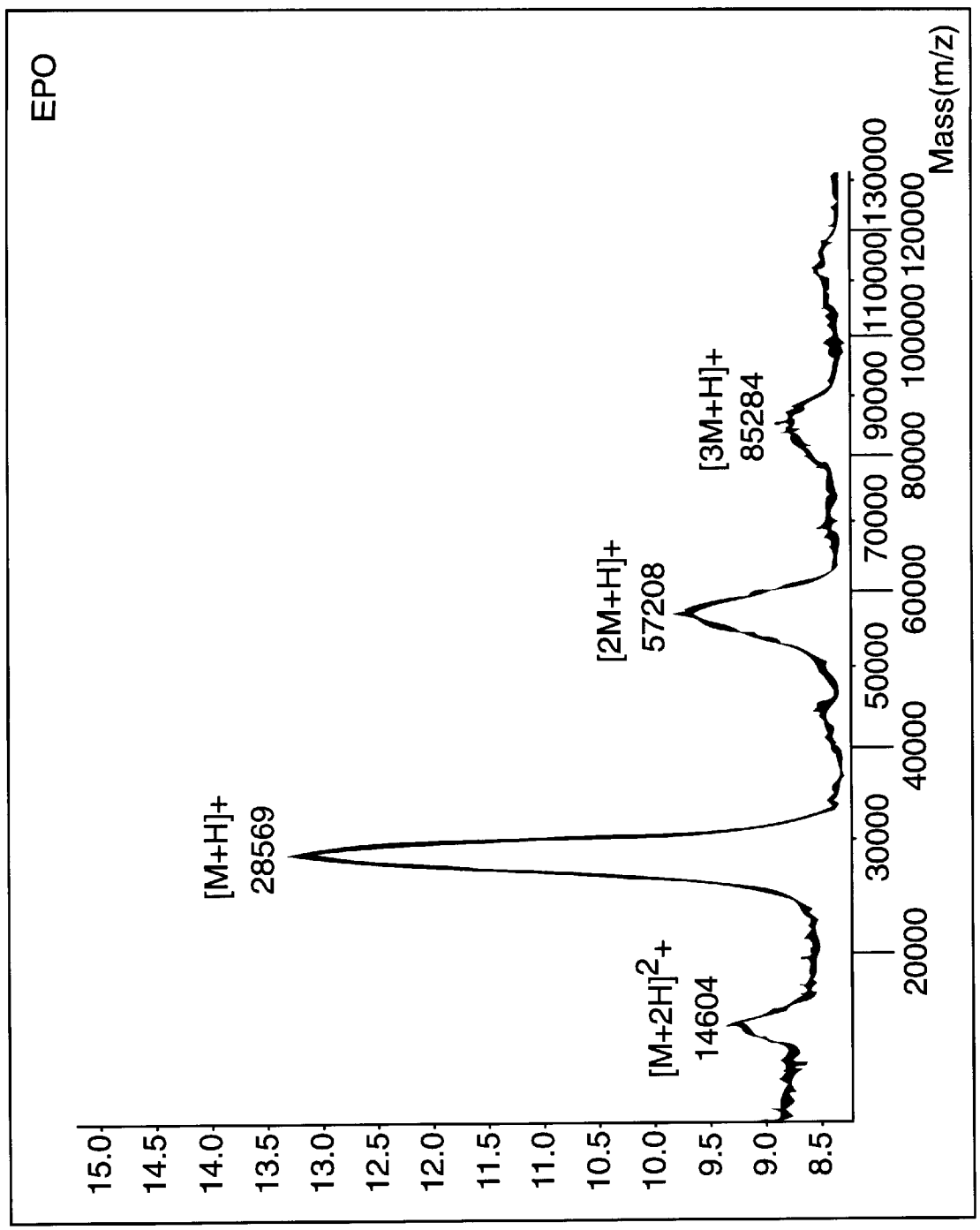
Figure 3C:
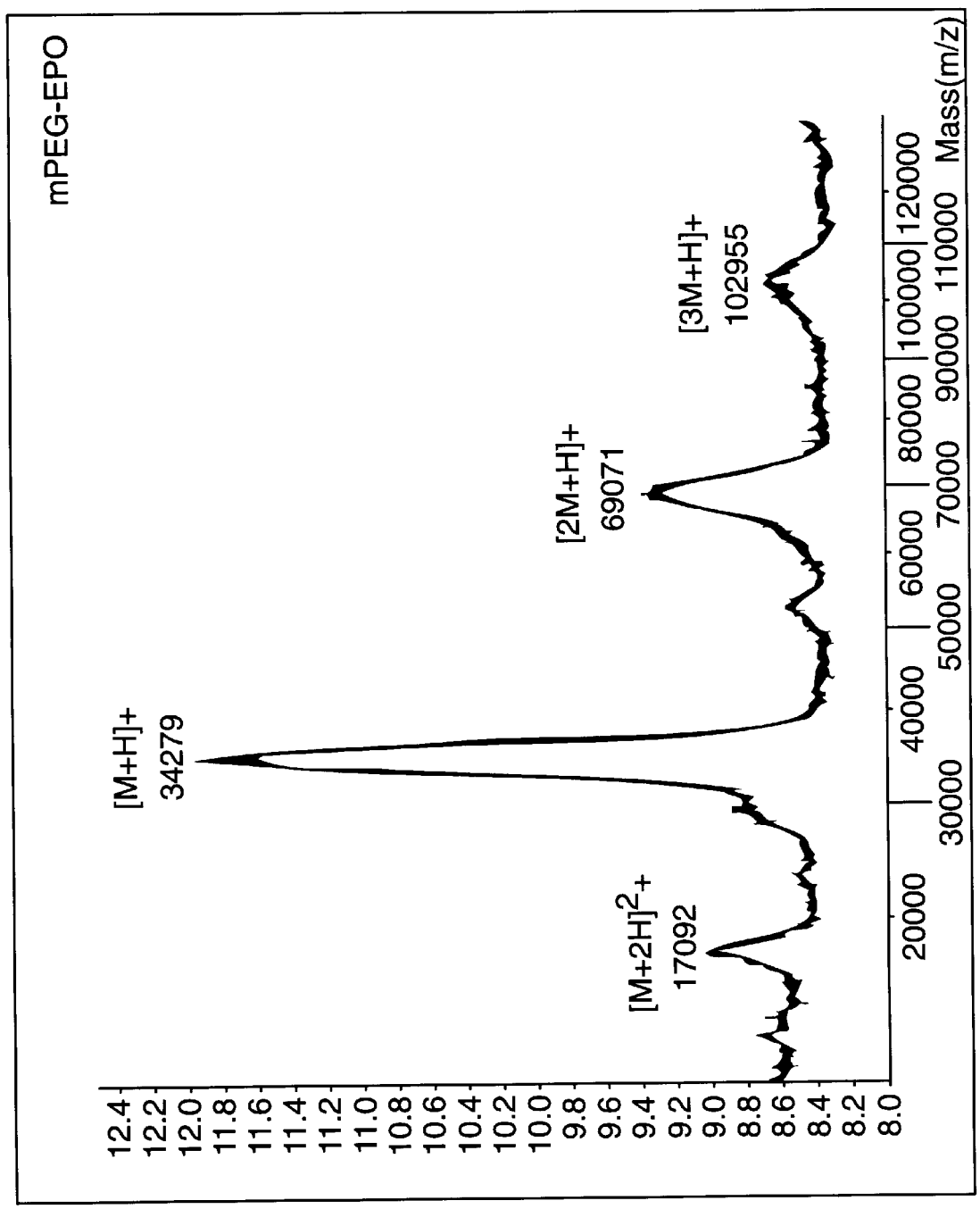
Figure 4A:
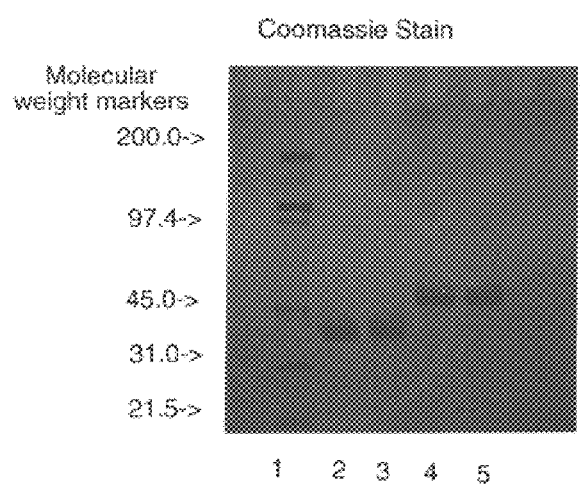
FIG. 4 shows the characterization of mPEG-EPO by electrophoresis methods: (1) 4–15% SDS-PAGE, Coomassie stain; (2) Western blot; (3) 4–15% SDS-PAGE, iodine stain; and (4) Isoelectric focusing (IEF, pH 3–7). Lane 1, MW or pI markers; Lane 2, native EPO; Lane 3, Transaminated EPO; and Lanes 4 and 5, mPEG-EPO with hydrazone bonds formed using hydrazine carboxylate (HZC) and hydrazide (HZ) moieties, respectively.
Figure 4B:
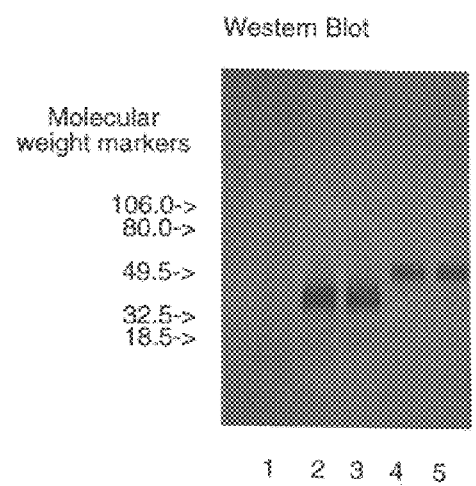
Figure 4C:
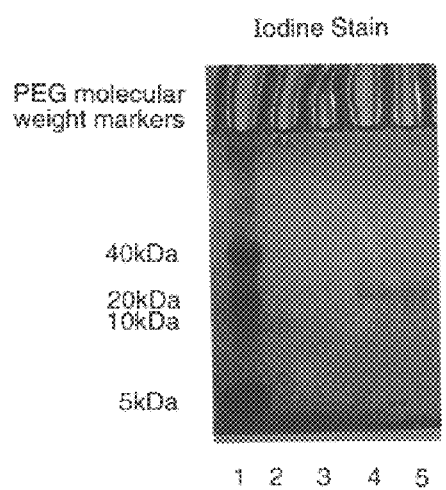
Figure 4D:
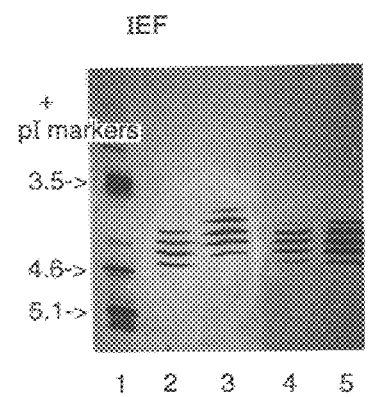

Matrix-assisted laser desorption mass spectrometry (Finnigan-MAT LaserMAT 2000, linear time-of-flight) was used to characterize mPEG-EPO by molecular weight determination (FIG. 3). mPEG5000 hydrazine carboxylate shows an ion at m/z 5157.4. EPO shows a two-charge monomer (m/z 14604), a one-charge monomer (m/z 28569), a dimer (m/z 57208) and a trimer (m/z 85284). Similarly, mPEG-EPO shows a two-charge monomer (m/z 17092), a one-charge monomer (m/z 34279), a direr (m/z 69071) and a trimer (m/z 102955).

A circular dichroism (CD) spectrum (Jobin-YVON CD6, Dichrograph Spectrometer Instruments, SA, Edison, N.J.) of mPEG-EPO showed that the protein retained the α-helical bundle structure present in native EPO (data not shown) This result means that a PEG molecule at the N-terminal end of EPO does not disrupt its secondary structure.

3. Preparation of mPEG-EPO with mPEG-hydrazide, mPEG-semicarbazide and oxylamine Transaminated EPO (1 mg) in 100 mM sodium acetate (pH 4.5) was adjusted to 0.5 M sodium chloride, 0.1% SDS to a final volume of 1 ml, and 10–20 mg of mPEG5000 hydrazide, semicarbazide or oxylamine were added. The reaction mixture was stirred for 40 hours at room temperature, and purified via a Sephacryl S-200 column (Pharmacia, Piscataway, N.J.) using a 20 mM sodium citrate (7.0) buffer containing 100 mM NaCl.

The mPEG-EPO conjugates were analyzed by 4–15% SDS-PAGE (Bio-Rad, Hercules, Calif.) with various methods: Coomassie stain (specific for proteins), Western blot (specific for EPO), and iodine stain (specific for PEG). The migration distance of higher molecular weight mPEG-EPO conjugates on SDS-PAGE is less than that of native EPO. The isoelectric focusing pattern indicates that the isoelectric point (pI) of EPO is not significantly altered upon modification. However, transaminated EPO is slightly more acidic than native EPO and mPEG-EPO.

Since the EPO and mPEG-EPO bands are well separated via SDS-PAGE, this technique can be used to monitor efficiency of the conjugation reaction. It was observed that the conjugation reaction was >95% complete when using mPEG5000-hydrazine carboxylate, whereas the reaction was only about 20% complete when using mPEG5000-hydrazide, mPEG5000-semicarbazide, or mPEG5000-oxylamine. Thus, the hydrazine carboxylate moiety appears to be more reactive towards carbonyl groups than is the hydrazide, semicarbazide, or oxylamine moiety.

4. Reactivity of mPEG-EPO with Anti-EPO Antibody

The antigenicity of mPEG-EPO was studied using a Quantikine™ IVD™ EPO ELISA kit (R&D systems, Minneapolis, Minn.). The assay consists of a microtiter plate coated with a monoclonal antibody to EPO. EPO or mPEG-EPO is allowed to interact with the coated plate. After washing the plate, a conjugate of anti-EPO polyclonal antibody and horseradish peroxidase is added. After removing excess conjugate, a chromogen is added to the wells and is oxidized by the enzyme reaction to form a blue colored complex. The absorbance of this complex is measured at 450 nm.

Figure 5:
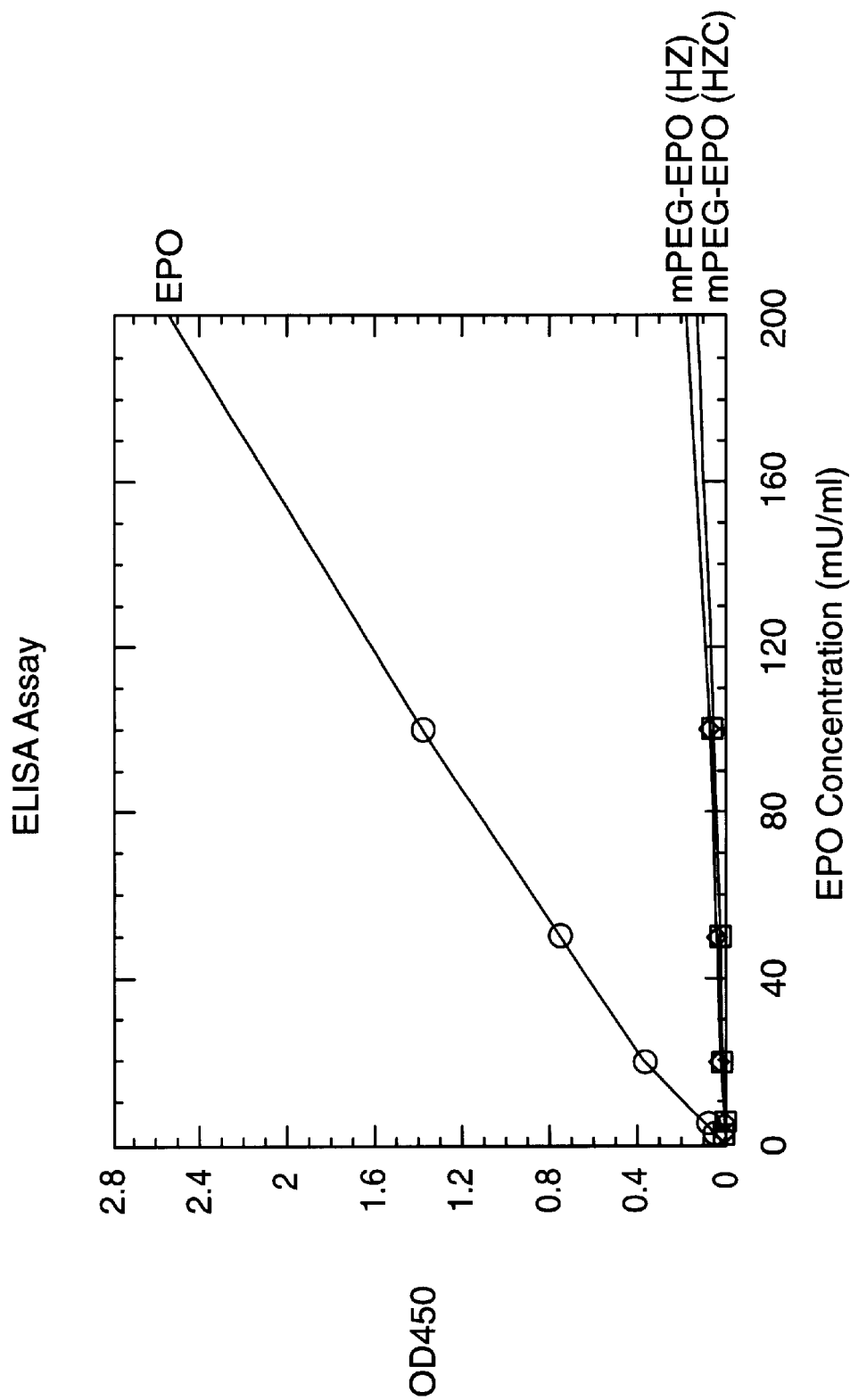
FIG. 5 shows a graph of results of an ELISA assay for mPEG-EPO with hydrazone bonds formed using hydrazine carboxylate (HZC) and hydrazide (HZ) moieties.

The results of the ELISA assay for mPEG-EPO with a hydrazone bond formed from hydrazine carboxylate (HZC) and hydrazide (HZ) are presented in FIG. 5. The data indicate that even one PEG molecule attached at the N-terminus of EPO significantly reduces the affinity of monoclonal antibody binding to EPO, possibly due to steric hindrance.

5. In vitro Activity of mPEG-EPO

The in vitro biological activity of mPEG-EPO was evaluated by a cell proliferation assay using FDC-P1/HER cells, a murine hematopoietic cell line. The cell line expresses the EPO receptor and is dependent on EPO for growth. After the cells are grown in the absence of EPO for 24 hours, EPO or mPEG-EPO was added to the cells. The cells were incubated for 42 hours, and then tritiated thymidine was added to the cells. After 6 hours, cell growth was determined by the incorporation of thymidine.

Figure 6:
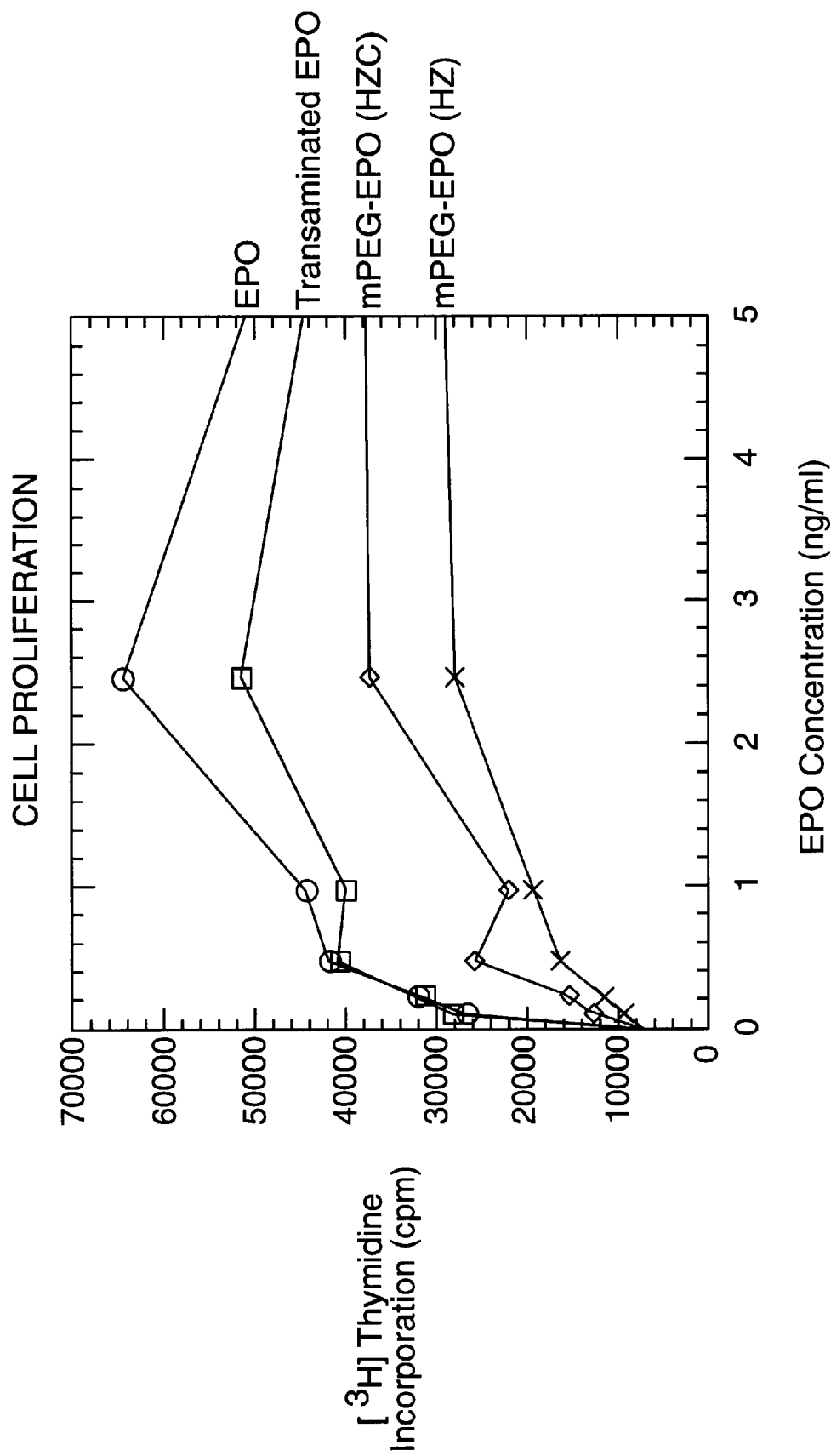
FIG. 6 shows a graph of the results of a cell proliferation assay of native EPO, transaminated EPO, and mPEG-EPO with hydrazone bonds formed using hydrazine carboxylate (HZC) and hydrazide (HZ) moieties.

The results of the cell proliferation assay for transaminated EPO and mPEG-EPO with hydrazone bonds formed from hydrazine carboxylate (HZC) and hydrazide (HZ) are presented in FIG. 6. Transaminated EPO shows full biological activity comparable to native EPO as determined by its $ED_{50}$. The mPEG-EPO samples with hydrazone bonds formed from hydrazine carboxylate (HZC) and hydrazide (HZ) only retain 38.5% and 25% activity, respectively, as determined by their $ED_{50}$. The data indicate that one PEG molecule attached at the N-terminus of EPO significantly reduces the affinity of EPO for its receptor, possibly due to steric hindrance.

6. In vivo Activity of mPEG-EPO

The in vivo activity of mPEG-EPO was evaluated by an exhypoxic mouse bioassay (Coates, P. M. et al., *Nature*, 1961, 191, 1065). Murine endogenous red cell formation is suppressed by the polycythemia produced through exposures to reduced pressure. The EPO or mPEG-EPO conjugate is injected at the level of 1 unit/mouse. Iron-59 was administered 48 hours after the EPO or mPEG-EPO injection. The iron-59 incorporation, which indicates new red blood cell formation, was measured 48, 72 and 96 hours after administration of EPO or mPEG-EPO.

The results of the exhypoxic mouse bioassay for mPEG-EPO with hydrazone bonds formed with hydrazine carboxylate (HZC), hydrazide (HZ) and semicarbazide (SCZ) are presented in FIG. 7. The mPEG-EPO samples show high in vivo activity as well as longer activity duration, compared to native EPO. The in vivo results indicate that mPEG-EPO samples have longer circulation time in vivo and sustained release of EPO during circulation.

7. Preparation of mPEG-Fibrin 17–29 Dimer

Fibrin 17–29 dimer has the following structure:

```
Gly-Pro-Arg-Val-Val-Glu-Arg-His-Gln-Ser-Ala-Cys-Lys
                                              |
                                              S
                                              |
                                              S
                                              |
Gly-Pro-Arg-Val-Val-Glu-Arg-His-Gln-Ser-Ala-Cys-Lys
```

2 mg of fibrin 17–29 dimer were dissloved in 0.5 ml of 2 M sodium acetate, 0.4 M acetic acid, 0.1 M glyoxylic acid, and 10 mM cupric sulfate (pH 5.5). The reaction was allowed to proceed for 2 hours at room temperature, and was stopped by adding 20 ml of 0.5 M EDTA. Transaminated fibrin dimer was purified via a Sephadex G-10 column (Pharmacia, Piscataway, N.J.) using a 100 mM sodium acetate (pH 4.5 buffer. Transaminated fibrin dimer showed significantly reduced Gly in the amino acid analysis, indicating the transamination of N-terminal Gly.

1 mg of transaminated fibrin dimer in 0.5 ml of 100 mM sodium acetate (pH 4.5) was added to 10 mg of mPEG5000 hydrazine carboxylate. The reaction mixture was stirred for 24 hours at room temperature. The mPEG-fibrin dimer was purified by anion-exchange chromatography with a HEMA IEC BIO CM column (Alltech). Mobile phase A was 20 mM sodium acetate (pH 5.5). Mobile phase B was 0.2 M MOPS, 0.05 M potassium phosphate mono-basic and 0.25 M potassium phosphate dibasic (pH 7.5). The gradient was 100% A for 5 minutes, then 0 to 100% B in 25 minutes. A new peak at 14.5 minutes, appearing before unmodified fibrin dimer (18 minutes), was collected for further analysis. A laser desorption mass spectrum showed the ion at m/z 8070.9, which proved that one PEG molecule was attached to the fibrin dimer (m/z 2986.8).

---

What is claimed is:

1. A method of covalently binding a water-soluble polymer to the N-terminal α-carbon atom of a polypeptide, which comprises the steps of
   (a) contacting the polypeptide with (i) glyoxylate ion or derivative thereof at a concentration of from about 0.1 M to about 2.0 M, (ii) a transition metal ion at a concentration of from about 10 μM to about 1 M, and (iii) a Lewis base at a concentration of from about 10 mM to about 10 M, at a pH of from about 3.0 to about 8.0 and a temperature of from about 0° C. to about 100° C., so as to form a transaminated polypeptide having an N-terminal α-carbonyl group; and
   (b) contacting the transaminated polypeptide, at a pH of from about 1.0 to about 7.5, with a water-soluble polymer having a moiety covalently bound thereto which reacts with the transaminated polypeptide's N-terminal α-carbonyl group to form a hydrazone bond, thereby covalently binding the polymer to the N-terminal α-carbon atom of the polypeptide, with the proviso that the polymer has a molecular weight of from about 200 to about 200,000 daltons, and the natural function of the polypeptide is not eliminated upon removal of its N-terminal α-amino group.

2. The method of claim 1, wherein the pH for step (a) is from about 5.0 to about 7.0.

3. The method of claim 1, wherein the pH for step (b) is from about 3.0 to about 5.0.

4. The method of claim 1, wherein the protein is EPO or derivative thereof.

5. The method of claim 1, wherein the polymer is PEG or derivative thereof.

6. The method of claim 5, wherein the PEG or derivative thereof has a molecular weight of from about 700 to about 20,000 daltons.

7. The method of claim 6, wherein the PEG or derivative thereof has a molecular weight of about 5,000 daltons.

8. The method of claim 1, wherein the moiety covalently bound to the polymer is hydrazine carboxylate.

9. The method of claim 1, wherein the protein is EPO, the polymer is mPEG having a molecular weight of about 5,000 daltons, and the moiety covalently bound to the polymer is hydrazine carboxylate.

10. The method of claim 1, which further comprises the step of reducing the hydrazone bond formed in step (b) so as to form a reduced hydrazone bond.

11. A kit for use in practicing the method of claim 1, which comprises the following:
   (a) a glyoxylate ion or derivative there of;
   (b) a transition metal ion;
   (c) a Lewis base; and
   (d) a water-soluble polymer having a molecular weight of from about 200 to about 200,000 daltons, and having a moiety covalently bound thereto which reacts with a transaminated polypeptide's N-terminal α-carbonyl group to form a hydrazone bond, thereby covalently binding the polymer to the N-terminal α-carbon atom of the polypeptide.

* * * * *

UNITED STATES PATENT AND TRADEMARK OFFICE
CERTIFICATE OF CORRECTION

PATENT NO.    : 6,077,939
DATED         : June 20, 2000
INVENTOR(S)   : Ziping Wei, Belle Mead; Sunitha Menon-Rudolph, Wuklingboro; Pradip Ghosh-Dastidar, Gladstone Page 1 of 1

It is certified that error appears in the above-identified patent and that said Letters Patent is hereby corrected as shown below:

Title page,
Item [22], Filed: August 1, 1997
Related U.S. Application Data: Provisional Application Serial No. 60/023,050 Filed August 2, 1996

Signed and Sealed this

Fifth Day of February, 2002

*Attest:*

JAMES E. ROGAN
*Director of the United States Patent and Trademark Office*

*Attesting Officer*

SEQUENCE LISTING

```
<160> NUMBER OF SEQ ID NOS: 12

<210> SEQ ID NO 1
<211> LENGTH: 20
<212> TYPE: PRT
<213> ORGANISM: Unknown
<220> FEATURE:
<223> OTHER INFORMATION: Description of Unknown Organism: peptide
      fragment

<400> SEQUENCE: 1

Gly Gly Leu Tyr Leu Cys Arg Phe Gly Pro Val Thr Trp Asp Cys Gly
 1               5                  10                  15

Tyr Lys Gly Gly
            20

<210> SEQ ID NO 2
<211> LENGTH: 20
<212> TYPE: PRT
<213> ORGANISM: Unknown
<220> FEATURE:
<223> OTHER INFORMATION: Description of Unknown Organism:peptide
      fragment

<400> SEQUENCE: 2

Gly Gly Thr Tyr Ser Cys His Phe Gly Pro Leu Thr Trp Val Cys Lys
```

-continued

```
                1               5                  10                 15
Pro Gln Gly Gly
            20

<210> SEQ ID NO 3
<211> LENGTH: 20
<212> TYPE: PRT
<213> ORGANISM: Unknown
<220> FEATURE:
<223> OTHER INFORMATION: Description of Unknown Organism:peptide
      fragment

<400> SEQUENCE: 3

Gly Gly Asp Tyr His Cys Arg Met Gly Pro Leu Thr Trp Val Cys Lys
 1               5                  10                 15
Pro Leu Gly Gly
            20

<210> SEQ ID NO 4
<211> LENGTH: 20
<212> TYPE: PRT
<213> ORGANISM: Unknown
<220> FEATURE:
<223> OTHER INFORMATION: Description of Unknown Organism:peptide
      fragment

<400> SEQUENCE: 4

Val Gly Asn Tyr Met Cys His Phe Gly Pro Ile Thr Trp Val Cys Arg
 1               5                  10                 15
Pro Gly Gly Gly
            20

<210> SEQ ID NO 5
<211> LENGTH: 20
<212> TYPE: PRT
<213> ORGANISM: Unknown
<220> FEATURE:
<223> OTHER INFORMATION: Description of Unknown Organism:peptide
      fragment

<400> SEQUENCE: 5

Gly Gly Val Tyr Ala Cys Arg Met Gly Pro Ile Thr Trp Val Cys Ser
 1               5                  10                 15
Pro Leu Gly Gly
            20

<210> SEQ ID NO 6
<211> LENGTH: 19
<212> TYPE: PRT
<213> ORGANISM: Unknown
<220> FEATURE:
<223> OTHER INFORMATION: Description of Unknown Organism:peptide
      fragment

<400> SEQUENCE: 6

Val Gly Asn Tyr Met Ala His Met Gly Pro Ile Thr Trp Val Cys Arg
 1               5                  10                 15
Pro Gly Gly

<210> SEQ ID NO 7
<211> LENGTH: 18
<212> TYPE: PRT
<213> ORGANISM: Unknown
<220> FEATURE:
<223> OTHER INFORMATION: Description of Unknown Organism:peptide
``` fragment

<400> SEQUENCE: 7

Gly Gly Thr Tyr Ser Cys His Phe Gly Pro Leu Thr Trp Val Cys Lys
 1               5                  10                  15

Pro Gln

<210> SEQ ID NO 8
<211> LENGTH: 20
<212> TYPE: PRT
<213> ORGANISM: Unknown
<220> FEATURE:
<223> OTHER INFORMATION: Description of Unknown Organism:peptide
      fragment

<400> SEQUENCE: 8

Gly Gly Leu Tyr Ala Cys His Met Gly Pro Met Thr Trp Val Cys Gln
 1               5                  10                  15

Pro Leu Arg Gly
            20

<210> SEQ ID NO 9
<211> LENGTH: 22
<212> TYPE: PRT
<213> ORGANISM: Unknown
<220> FEATURE:
<223> OTHER INFORMATION: Description of Unknown Organism:peptide
      fragment

<400> SEQUENCE: 9

Thr Ile Ala Gln Tyr Ile Cys Tyr Met Gly Pro Glu Thr Trp Glu Cys
 1               5                  10                  15

Arg Pro Ser Pro Lys Ala
            20

<210> SEQ ID NO 10
<211> LENGTH: 13
<212> TYPE: PRT
<213> ORGANISM: Unknown
<220> FEATURE:
<223> OTHER INFORMATION: Description of Unknown Organism:peptide
      fragment

<400> SEQUENCE: 10

Tyr Ser Cys His Phe Gly Pro Leu Thr Trp Val Cys Lys
 1               5                  10

<210> SEQ ID NO 11
<211> LENGTH: 11
<212> TYPE: PRT
<213> ORGANISM: Unknown
<220> FEATURE:
<223> OTHER INFORMATION: Description of Unknown Organism:peptide
      fragment

<400> SEQUENCE: 11

Tyr Cys His Phe Gly Pro Leu Thr Trp Val Cys
 1               5                  10

<210> SEQ ID NO 12
<211> LENGTH: 13
<212> TYPE: PRT
<213> ORGANISM: Unknown
<220> FEATURE:
<223> OTHER INFORMATION: Description of Unknown Organism:peptide
      fragment -continued

```
<400> SEQUENCE: 12

Gly Pro Arg Val Val Glu Arg His Gln Ser Ala Cys Lys
1               5                   10
```